(12) United States Patent
Stangenes et al.

(10) Patent No.: US 8,460,286 B2
(45) Date of Patent: Jun. 11, 2013

(54) CONFORMING ELECTRODE

(75) Inventors: Todd Stangenes, Minneapolis, MN (US); Saurav Paul, Minnetonka, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1537 days.

(21) Appl. No.: 11/967,457

(22) Filed: Dec. 31, 2007

(65) Prior Publication Data

US 2008/0140072 A1    Jun. 12, 2008

Related U.S. Application Data

(63) Continuation-in-part of application No. 11/953,151, filed on Dec. 10, 2007, which is a continuation of application No. 10/808,919, filed on Mar. 24, 2004, now Pat. No. 7,326,204, application No. 11/967,457, which is a continuation-in-part of application No. 11/617,397, filed on Dec. 28, 2006, now Pat. No. 7,819,870, which is a continuation-in-part of application No. 11/553,965, filed on Oct. 27, 2006, now Pat. No. 8,021,361.

(60) Provisional application No. 60/537,092, filed on Jan. 16, 2004, provisional application No. 60/730,634, filed on Oct. 27, 2005.

(51) Int. Cl.
*A61B 18/14* (2006.01)

(52) U.S. Cl.
USPC ............................................. 606/41; 607/99

(58) Field of Classification Search
USPC ............ 600/373; 606/40, 49, 47, 41; 607/99, 607/102, 115
See application file for complete search history.

(56) References Cited

U.S. PATENT DOCUMENTS

| | | | |
|---|---|---|---|
| 4,358,669 A | 11/1982 | Bryson, Jr. et al. | |
| 4,358,699 A | 11/1982 | Wilsdorf | |
| 4,415,635 A | 11/1983 | Wilsdorf et al. | |
| 4,773,413 A | 9/1988 | Hussein et al. | |
| 4,998,933 A | 3/1991 | Eggers et al. | |
| 5,222,949 A * | 6/1993 | Kaldany | 604/524 |
| 5,676,693 A | 10/1997 | LaFontaine | |
| 5,944,715 A | 8/1999 | Goble et al. | |
| 6,013,076 A * | 1/2000 | Goble et al. | 606/41 |
| 6,015,406 A | 1/2000 | Goble et al. | |
| 6,015,407 A | 1/2000 | Rieb et al. | |
| 6,047,700 A | 4/2000 | Eggers et al. | |
| 6,053,937 A * | 4/2000 | Edwards et al. | 607/104 |
| 6,090,106 A | 7/2000 | Goble, Jr. et al. | |
| 6,109,268 A | 8/2000 | Thapliyal et al. | |
| 6,168,594 B1 | 1/2001 | LaFontaine et al. | |
| 6,183,469 B1 | 2/2001 | Thapliyal et al. | |

(Continued)

*Primary Examiner* — Michael Peffley
*Assistant Examiner* — Thomas Giuliani
(74) *Attorney, Agent, or Firm* — Wiley Rein LLP (57) ABSTRACT

A conforming electrode for delivering ablative energy to tissue generally includes a plurality of flexible metal tubes, each having a longitudinal axis, a proximal end, and a distal end. The flexible metal tubes are arranged in a bundle with their longitudinal axes aligned parallel to each other. In addition, the flexible metal tubes are electrically coupled to a conductor for transferring ablative energy to the flexible metal tubes. The conductor may be a loop around the flexible metal tubes and to which the flexible metal tubes may be secured. The proximal ends of the flexible metal tubes may be secured to the distal end of a catheter shaft.

20 Claims, 10 Drawing Sheets

U.S. PATENT DOCUMENTS

| | | | |
|---|---|---|---|
| 6,231,570 B1 * | 5/2001 | Tu et al. | 606/41 |
| 6,298,257 B1 | 10/2001 | Hall et al. | |
| 6,302,903 B1 * | 10/2001 | Mulier et al. | 607/105 |
| 6,363,937 B1 | 4/2002 | Hovda et al. | |
| 6,402,745 B1 | 6/2002 | Wilk | |
| 6,416,514 B1 | 7/2002 | Ein-Gal | |
| 6,516,230 B2 * | 2/2003 | Williams et al. | 607/116 |
| 6,585,732 B2 | 7/2003 | Mulier et al. | |
| 6,622,731 B2 | 9/2003 | Daniel et al. | |
| 6,652,515 B1 | 11/2003 | Maguire et al. | |
| 6,660,002 B1 * | 12/2003 | Edwards et al. | 606/41 |
| 6,780,180 B1 * | 8/2004 | Goble et al. | 606/41 |
| 6,855,143 B2 * | 2/2005 | Davison et al. | 606/41 |
| 6,881,213 B2 * | 4/2005 | Ryan et al. | 606/41 |
| 7,063,698 B2 * | 6/2006 | Whayne et al. | 606/49 |
| 7,171,275 B2 * | 1/2007 | Hata et al. | 607/122 |
| 7,326,204 B2 * | 2/2008 | Paul et al. | 606/41 |
| 7,326,205 B2 * | 2/2008 | Paul et al. | 606/41 |
| 7,326,206 B2 | 2/2008 | Paul et al. | |
| 2001/0024735 A1 * | 9/2001 | Kuhlmann-Wilsdorf et al. | 428/611 |
| 2001/0032001 A1 | 10/2001 | Ricart et al. | |
| 2002/0010463 A1 | 1/2002 | Mulier et al. | |
| 2004/0231683 A1 | 11/2004 | Eng et al. | |
| 2005/0267467 A1 * | 12/2005 | Paul et al. | 606/41 |

* cited by examiner

CONFORMING ELECTRODE

CROSS-REFERENCE TO RELATED APPLICATIONS

This application is a continuation-in-part of U.S. application Ser. No. 11/953,151, filed 10 Dec. 2007, currently pending, which is a continuation of U.S. application Ser. No. 10/808,919, filed 24 Mar. 2004, now U.S. Pat. No. 7,326,204, which claims the benefits of United States provisional application No. 60/537,092, filed 16 Jan. 2004. This application is also a continuation-in-part of U.S. application Ser. No. 11/617,397, filed 28 Dec. 2006, now U.S. Pat. No. 7,819,870, which is a continuation-in-part of U.S. application Ser. No. 11/553,965, filed 27 Oct. 2006 now U.S. Pat. No. 8,021,361, which claims the benefit of United States provisional application No. 60/730,634, filed 27 Oct. 2005. Each of these applications is hereby incorporated by reference as though fully set forth herein.

BACKGROUND OF THE INVENTION

A. Field of the Invention

The instant invention is directed toward a conforming electrode and a method for using the conforming electrode for tissue ablation. In particular, the conforming electrode of the present invention comprises a plurality of flexible filaments or bristles which may be used for applying ablative energy (e.g., RF energy) to target tissue during the formation of spot or continuous linear lesions.

B. Background Art

It is well known that benefits may be gained by forming lesions in tissue if the depth and location of the lesions being formed can be controlled. In particular, it can be desirable to elevate tissue temperature to around 50° C. until lesions are formed via coagulation necrosis, which changes the electrical properties of the tissue. For example, when good or sufficiently deep lesions are formed at specific locations in cardiac tissue via coagulation necrosis, undesirable atrial fibrillations may be lessened or eliminated. The definition of "good" or "sufficiently deep" lesions depends at least to some extent on the procedure and may also depend on other considerations such as tissue characteristics. "Sufficiently deep" lesions means transmural lesions in some cardiac applications.

Several difficulties may be encountered, however, when attempting to form adequately-deep lesions at specific locations using some existing ablation electrodes. For example, when forming lesions with RF energy, high temperature gradients are often encountered in the vicinity of the electrode. At the edges of some existing electrodes are regions of very high current density, leading to large temperature gradients and hot spots. These "edge effects" may result in the formation of undesirable coagulum and charring of the surface tissue. For example, undesirable coagulum may begin to form when blood reaches around 80° C. for an appreciable length of time, and undesirable tissue charring and desiccation may be seen when tissue reaches around 100° C. for an appreciable length of time. There are two types of undesirable coagulum: coagulum that adheres to and damages the medical device; and coagulum blood clots or curds that may enter a patient's bloodstream, possibly resulting in other health problems for the patient. Charring of the surface tissue may also have deleterious effects on a patient.

As the temperature of the electrode is increased, the contact time required to form an adequately-deep lesion decreases, but the likelihood of charring surface tissue and forming undesirable coagulum increases. As the temperature of the electrode is decreased, the contact time required to form an adequately-deep lesion increases, but the likelihood of charring surface tissue and forming undesirable coagulum decreases. It is, therefore, a balancing act trying to ensure that tissue temperatures are adequately high for long enough to create deep lesions, while still preventing or minimizing coagulum formation and/or charring of the surface tissue. Active temperature control may help, but the placement of thermocouples, for example, is tricky and setting the RF generator for a certain temperature becomes an empirical exercise as actual tissue temperatures are generally different from those recorded next to the electrode due to factors such as convection and catheter design.

Thus, there remains a need for effective thermal control during ablation procedures.

Another difficulty encountered with existing ablation electrodes is how to ensure adequate tissue contact. Current techniques for creating continuous linear lesions in endocardial applications include, for example, dragging a conventional catheter on the tissue, using an array electrode, or using pre-formed electrodes. All of these devices comprise rigid electrodes that do not always conform to the tissue surface, especially when sharp gradients and undulations are present, such as at the ostium of each pulmonary vein in the left atrium and the isthmus of the right atrium. Consequently, continuous linear lesions are difficult to achieve. When forming lesions in a heart, the beating of the heart further complicates matters, making it difficult to keep adequate contact between the electrode and the tissue for a sufficient length of time to form a desired lesion. With a rigid electrode, it can be quite difficult to maintain sufficient contact pressure until an adequate lesion has been formed. This problem is exacerbated on contoured or trabeculated surfaces. If the contact between the electrode and the tissue cannot be properly maintained, a quality lesion is unlikely to be formed.

Catheters based upon a virtual electrode may address some of the difficulties, but these catheters often require high flow rates of conductive fluid (e.g., typically around 70 milliliters per minute) to maintain effective cooling for high-power RF applications. The introduction of a large amount of conductive fluid into a patient's bloodstream may have detrimental effects on the patient.

Brush electrodes containing flexible electrode filaments provide certain advantages, particularly in maintaining effective contact on irregular surfaces. Brush electrodes for ablation are known in the art but have been predominantly limited to arthroscopic procedures for vaporizing tissue. For example, Goble, et al., U.S. Pat. Nos. 5,944,715 and 6,780,180 disclose a number of examples of brush electrodes consisting of flexible metal fibers. However, arthroscopic ablation devices such as Goble are specifically designed to operate in articular joints filled with synovial fluids. The term "underwater surgery" is frequently used to describe these procedures. Under such conditions, large amounts of fluid may be introduced into the working surface without detrimental effects. However, as noted above, for catheters designed to work in vascular environments, the introduction of large quantities of conductive fluids into a patient's bloodstream is not desirable.

Previous disclosures have sought to address some of the difficulties associated with the use of brush electrodes in vascular environments. For example, in U.S. application Ser. No. 10/808,919, to which this application claims priority, an exemplary brush electrode comprised of about 2000 flexible filaments is disclosed. The filaments comprise part of a catheter with an outer sheath that surrounds the fibers and provides mechanical support for the flexible filaments. The sheath may also provide electrical shielding. The flexible filaments typically project a few millimeters from the distal end of the outer sheath. Conductive fluid such as saline may be provided to the distal end of the brush via interstitial spaces between the filaments. Additional embodiments may include hollow fibers, which can provide (and control) fluid to the target site via the additional paths through the fibers.

The advantages of using brush electrodes with small filaments and/or hollow passages in vascular environments are several. By providing many more filaments than in a typical arthroscopic brush, the total surface area of the working surface is greatly increased. Increased surface area dramatically increases the uniformity of energy transfer to a tissue site, greatly reducing the "edge effects" associated with traditional ablation electrodes as described above. Additionally, the increased surface area also dramatically increases the amount of heat transfer away from target tissue, allowing increased ablation times and reduced negative effects such as "charring" or coagulation of blood.

Advantageously, in vascular applications, the increased surface area available for cooling in brush electrodes with multiple small fibers means that the cooling fluid introduced into the fibers also transfers heat much more effectively. Thus, the total amount of cooling fluid required during a particular procedure may be greatly reduced and the undesirable medical consequences of introducing too much fluid into the vascular system at one time may be avoided.

Although the results associated with tests of brush electrodes such as those described above represent dramatic improvements in electrical and thermal performance, there remain additional design challenges to introducing these devices into vascular environments such as the heart.

It is desirable to minimize the risk that debris may be introduced to the body during surgery. One way to reduce this risk is to use instruments having fewer parts. In addition to minimizing the opportunity for debris to be introduced into the blood stream, using fewer parts allows for comprehensive accountability of parts when they are introduced and ultimately removed from the body.

Thus, there remains a need for conforming electrode catheters that address issues with existing designs and still permit the formation of uniform, transmural spot and continuous linear lesions on smooth or contoured surfaces in a manner that is safe and effective when used in vascular environments such as the heart.

BRIEF SUMMARY OF THE INVENTION

It is desirable to be able to form adequately-deep spot or continuous linear lesions in tissue while applying a reasonable amount of RF energy. It is further desired to reduce the formation of undesirable coagulum and charring of the surface tissue. This can be accomplished by providing conforming electrodes with sufficient cooling fluid and surface area to control the intensity and duration of heating during the procedure. The amount of cooling fluid applied during the procedure must also be controlled in order to prevent the undesirable medical consequences of introducing too much fluid into the vascular system over a short period of time.

It is also desirable to provide a catheter with improved conforming electrodes that securely attach the individual elements of the conforming electrode to the catheter in a manner that does not adversely affect the electrical and thermal characteristics which represent the advantages of using brush electrodes.

In a first aspect according to the present teachings, a conforming electrode is provided that can deliver ablative energy.

The conforming electrode may have a plurality of flexible metal tubes each having a longitudinal axis, a proximal end and a distal end, with the tubes arranged in a bundle with their longitudinal axes aligned parallel to each other, and electrically coupled to a conductor for transferring ablative energy. The flexible tubes may be formed from, for example, NITINOL (shape memory alloy of nickel and titanium). It is contemplated that the tubes may be secured to each other. It is specifically contemplated that the tubes could be welded to each other at their proximal ends. The welding could be done with a laser or with other welding techniques. Alternatively, or in addition, the proximal ends of the tubes could be secured to the distal end of a catheter shaft. In some embodiments, the conductor may form a loop around the plurality of flexible tubes to additionally secure the tubes to the conductor.

It is within the scope of the present teachings to include an electrode housing coupled to the distal end of the catheter shaft; wherein the plurality of flexible tubes are secured to each other at their proximal ends and are also secured to the electrode housing. The electrode housing could be a conductive sheath.

As taught herein, at least some of the plurality of flexible tubes may have helical cuts extending through their walls along their longitudinal axes. The helical cuts could be continuous along the length of the tube or be a plurality of non-continuous cuts. The plurality of flexible tubes may be arranged in a bundle which form interstitial spaces between the flexible tubes. Additionally, the conforming electrode could have a fluid lumen that is adapted to deliver fluid to the interstitial spaces between the flexible tubes.

It is within the scope of the present teachings for the conforming electrode to include a catheter shaft having a fluid lumen to deliver a fluid. Furthermore, a manifold may be coupled to the fluid lumen and to at least some of the plurality of flexible tubes to deliver fluid to the interiors of the flexible tubes. It is further contemplated that a sensor may be embedded among the plurality of flexible tubes. The sensor could be an electrical, thermal, or contact sensor. Furthermore, the sensor may be embedded within at least one of the plurality of flexible tubes.

Another aspect of the present teachings relates to an ablation catheter having an ablating electrode with a plurality of flexible metal tubes each of which has a longitudinal axis, a proximal end, and a distal end. At least some of the tubes can have helical cuts extending through the walls of the tubes along their longitudinal axes and be arranged in a bundle with their longitudinal axes aligned parallel to each other. The tubes may be secured to one another and also may be electrically coupled to a conductor for transferring ablative energy.

Yet another aspect of the present teachings pertains to a method of manufacturing a conforming electrode having a plurality of flexible metal tubes each having a longitudinal axis, a proximal end, and a distal end. At least one helical cut may be made through the wall of at least one of the flexible tubes along its longitudinal axis. In some embodiments the plurality of flexible tubes may be arranged into a bundle with their longitudinal axes aligned parallel to one another. It is contemplated that flexible tubes may be secured to each other at their proximal ends. The method may also provide for securing the proximal ends of the flexible tubes to the catheter shaft itself. The flexible tubes may be secured to each other or to the catheter shaft by welding. It is additionally contemplated that the helical cuts may be made by a laser. Alternatively, the helical cuts could be made by mechanical cutting.

The foregoing and other aspects, features, details, utilities, and advantages of the present invention will be apparent from reading the following description and claims, and from reviewing the accompanying drawings.

DETAILED DESCRIPTION OF EMBODIMENTS OF THE INVENTION

Figure 1:
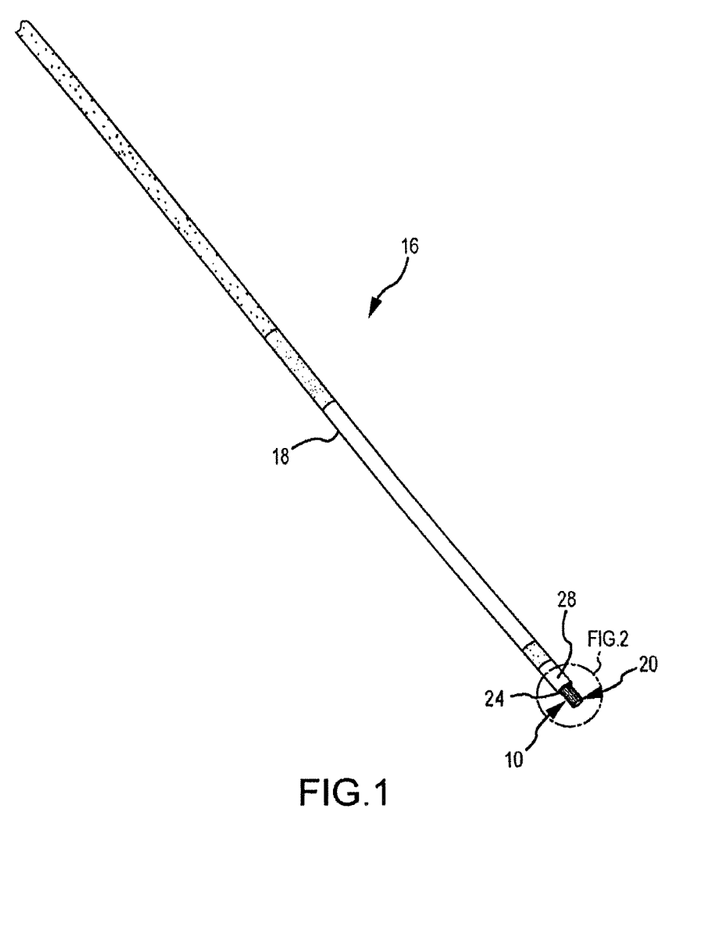
FIG. 1 is an isometric view of one embodiment of a catheter having a conforming electrode according to the present teachings, and depicts the filaments comprising the conforming electrode extending from a distal end of an outer sheath.

FIG. 1 is an isometric view of one embodiment of a catheter 16 having a conforming electrode 10 according to the present teachings. As depicted in this figure, the catheter comprises a catheter shaft with an outer sheath 18. In the embodiment depicted in FIG. 1, the outer sheath is formed from sections of different material (e.g., in the embodiment depicted FIG. 1, five different sections comprise the outer sheath). These sections of different material enable the catheter 16 to have, for example, different mechanical properties (e.g., flexibility) at different locations along the catheter shaft. The outer sheath 18 may or may not comprise these sections of different material depending upon the intended application for the catheter. Although the outer sheath 18 depicted in FIG. 1 has a circular cross section, the cross section of the outer sheath may be other than circular.

Figure 2:
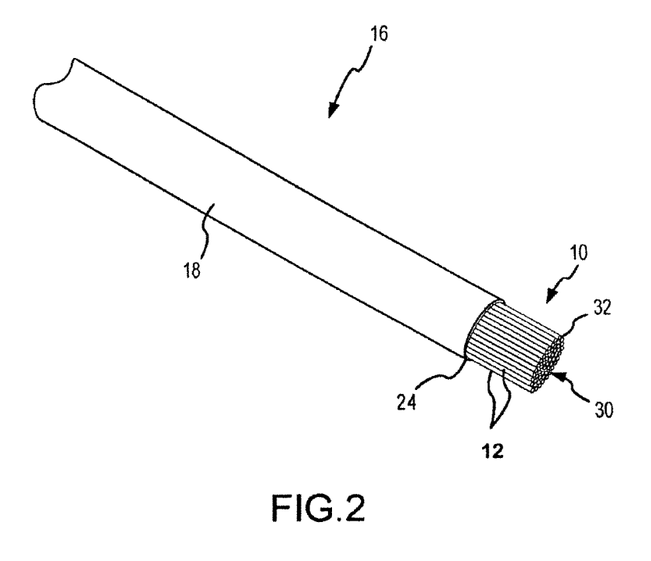
FIG. 2 is an enlarged view of the circled region of FIG. 1.
Figure 3:
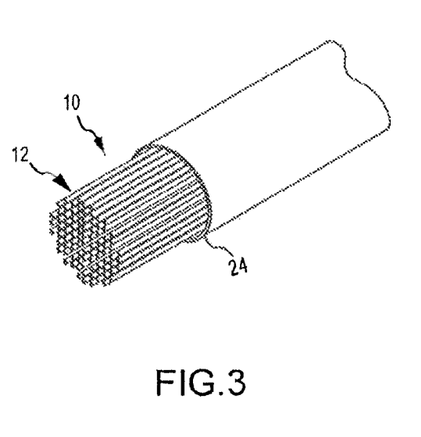
FIG. 3 is a detailed view of the working surface of the conforming electrode of FIGS. 1-2 which shows the individual filaments comprising flexible metal tubes.

As also shown in FIGS. 1-3, the conforming electrode 10, which comprises an exposed portion 20 and an embedded portion (not shown), is present at a distal end 24 of the outer sheath 18. In particular, at the distal end of the outer sheath, the exposed portion 20 of the conforming electrode 10, comprising a plurality of filaments 12, may be seen (see, e.g., FIG. 2). The exposed portion of the conforming electrode may project a few millimeters from the distal end of the outer sheath. The distance that the exposed portion of the conforming electrode extends from the distal end of the outer sheath may vary depending upon a number of factors including the composition of the filaments comprising the conforming electrode 10 and the particular area to be treated. The distal end 24 of the outer sheath 18 may include a conductive or nonconductive base 28. The flexible conforming electrode provides enhanced tissue contact, particularly for use on contoured or trabeculated surfaces.

FIG. 2 is an enlarged view of the circled region of FIG. 1—the "working surface." As clearly shown in FIG. 2, the conforming electrode 10 according to this embodiment has a relatively flat working surface 30 at the distal end 32 of the conforming electrode 10. In other words, in this depicted embodiment, all of the filaments 12 comprising the conforming electrode 10 extend approximately the same distance from the distal end 24 of the outer sheath 18. Thus, the conforming tip provides a relatively flat working surface 30 comprising the longitudinal ends of the filaments. The outer sheath of the catheter may provide mechanical support for the filaments and may also provide electrical shielding.

Generally, the conforming electrode comprises a plurality of flexible fibers arranged in a bundle at a distal end of a sheath. The plurality of flexible fibers shown with a flat working surface in FIG. 2 may extend beyond the distal end of the sheath in a variety of different lengths, depending upon the desired application. For instance, the greater the length of the exposed fibers, the greater the flexibility the fibers exhibit at their working surface. Conversely, the shorter the distance the fibers extend beyond the distal end of the sheath, the more rigid the working surface becomes. Increasing the rigidity of the working surface in this manner also increases the resilience or elasticity of the working surface, allowing it to more easily restore itself back to its original shape following contact with a tissue surface.

The present teachings also contemplate that the sheath 18 may be configured to be extendable over the flexible filaments. Such a configuration permits the length of the exposed fibers to be adjusted during a medical procedure by extending or retracting the sheath over the flexible fibers 12. This allows for adjustment of the flexibility and elasticity of the fibers during a procedure depending on the desired characteristics.

FIG. 3 shows a further exemplary embodiment of the conforming electrode 10 according to the present teachings. The flexible filaments shown in FIG. 3 are comprised of a plurality of flexible tubes 12 arranged in a bundle and surrounded by a sheath 24. The flexible tubes 12 may be constructed from any of a wide variety of materials, including conductive materials and semi-conductive materials. Exemplary materials include, but are not limited to, metal fibers and metal-plated fibers (e.g., metal-plated carbon-compound fibers, acrylic fibers, and nylon fibers). Preferably, the filaments comprise flexible metal tubes of NITINOL (shape memory alloy of nickel and titanium), gold, silver, platinum, iridium, or stainless steel.

In one embodiment, the flexible tubes 12 may be made of a metal fiber such as NITINOL (shape memory alloy of nickel and titanium). NITINOL is known in the art for its properties of high elasticity, flexibility, biocompatibility, and electrical performance. Other metals also suitable for conforming electrodes according to the present teachings may include, for example, gold, platinum, titanium, and iridium. One skilled in the art will also appreciate that there are a number of metallic alloys that may be formed from combinations of these metals depending on the particular performance characteristics desired for the tubes.

It may be desirable to mix flexible tubes having different materials and properties within a single conforming electrode. For instance, in addition to flexible metal tubes made of conductive material, it may be desirable to add non-conductive fibers or tubes among the conductive tubes. Such a configuration may permit full realization of the advantages of the cooling effects of multiple tubes while still precisely controlling the ablation patterns associated with the conductive metal tubes.

Figure 6:
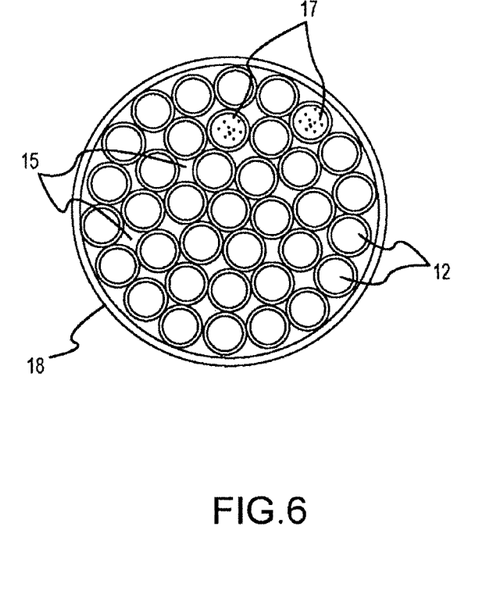
FIG. 6 depicts a cross-sectional view of a conforming electrode arrangement comprising thirty-seven flexible metal tubes.

For purposes of best mode, a particular embodiment (FIG. 6) of the plurality of flexible metal tubes 12 may comprise a total of 37 tubes having an outer diameter of approximately 0.136 inches and bundled in a manner that creates a 7-9 French catheter tip. The plurality of flexible metal tubes 12 may further comprise an inner diameter of 0.009 inches. It is noted, however, that any number of flexible tubes 12 may be used, depending on the desired size and characteristics of the catheter tip. Additionally, the outer diameter of the flexible metal tubes may be increased or decreased to accommodate fewer or more tubes as desired for a particular application. The inner diameter of the flexible metal tubes may likewise be varied depending on the desired characteristics.

Design factors influencing the size of the outer diameter of the tube may include the flexibility and elasticity desired for the fiber, the number of fibers desired for a particular bundle, the overall diameter of a surgical instrument desired for a particular application or environment, the type of mechanical attachment that will be made between the tubes and the surgical instrument, and the limits of various manufacturing techniques. Exemplary design variables related to choosing an inner diameter of the tube may include the amount of fluid desired to flow through the tube; the desired mechanical properties of the tube including its structural integrity, flexibility, and elasticity; and the limits of various manufacturing techniques.

Optionally, the flexible tubes 12 may be coated with conductive material. In addition, the flexible tubes 12 may be insulated from each other, or they may be in electrical contact with each other. Conductive or nonconductive fluids may flow through the tubes 12 or along the outer surface of the tubes 12 or both. The electrical conductivity of the individual filaments may be constant along the length of the filaments or may vary along the length of the filaments. Also, when it is desired to have the conductivity of a filament vary along its length, it may vary continuously or discontinuously.

Figure 4:
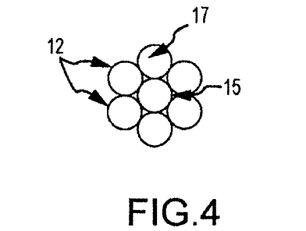
FIGS. 4-5 depict cross-sectional views of alternative arrangements of the flexible metal tubes.
Figure 5:
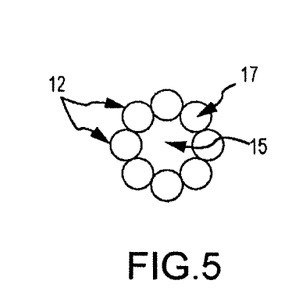

The flexible metal tubes may be bundled in a variety of arrangements depending on the physical characteristics desired. FIGS. 4 and 5 schematically depict two of the many possible bundled arrangements. FIG. 4 depicts an arrangement in which the flexible tubes 12 are bundled in a manner that minimizes the amount of space between the tubes. It will be immediately appreciated that even in a tightly packed configuration, interstitial spaces 15 are formed between the filaments.

The interstitial spaces 15 provide paths for the controlled flow of fluid among the tubes. The interstitial spaces 15 in FIG. 4, while relatively small in cross section, may run along an entire longitudinal length between fibers. By providing a plurality of tubes employing the tightly packed configuration, a relatively large surface area is provided for the fluid flow.

The relatively large surface area provided by the long, narrow interstitial spaces greatly increases heat transfer from an ablation site to fluid flowing along the fibers. Where cooling of the ablation site is desired, the comparatively large surface area created by the long, narrow interstitial spaces between the fibers advantageously decreases the need for large volumes of cooling fluid that may have undesirable effects in the blood stream.

When conductive fluid is used, the conforming electrode 10 may become a "wet-brush" electrode. In a wet-brush electrode, the conductive fluid serves both thermodynamic functions and electrical functions. Thermodynamically, the conductive fluid cools both the electrode and the tissue surface. Effective cooling of the electrode inhibits or prevents coagulum formation on the electrode; and effective cooling of the tissue surface permits longer application of relatively high ablative energy, resulting in the formation of deeper lesions. Electrically, the conductive fluid serves as a virtual electrode. The conductive fluid may also help to isolate the conductive conforming tubes from the surrounding blood, which helps prevent the formation of coagulum.

The conductive fluid also creates a conductivity gradient resulting from a concentration gradient. The conductive fluid flowing through the flexible tube interstitium has a field homogenizing effect. The conductive fluid flowing through the working surface at the distal tip of the wet-brush electrode thus helps to mitigate hot spots resulting from edge effects. Further, since the number of edges present in a conforming electrode, like the electrode according to the present teachings, greatly exceeds the number of edges present in many existing electrodes, the energy build up at each filament edge in the conforming electrode is less than it would be for existing electrodes, assuming the same power setting. This results in less severe edge effects when using the conforming electrode of the present teachings. The conductive fluid, when used, further smoothes or reduces the undesirable edge effects.

The packing density of the conforming electrode affects the interstitial spaces between the filaments. Where additional fluid flow is desired between the metal tubes 12, an arrangement such as that found in FIG. 5 is also possible. FIG. 5 depicts an alternate arrangement having a less densely packed bundle of tubes 12. This arrangement forms a larger interstitial space 15 through the center of the bundle. The larger interstitial space 15 allows for a greater amount of fluid flow into the conforming electrode if desired.

One of skill in the art will also immediately recognize that the hollow interiors 17 of the metal tubes 12 as shown in FIGS. 4 and 5 also provide conduits through which fluid may flow. The amount of flow through the hollow tubes 17 may be further controlled by increasing or decreasing the inner tube diameters. The flow through various cross sections of the conforming electrode may also be controlled by providing flexible tubes having different inner diameters within the bundle.

The fluid flowing through the interstitial spaces between flexible tubes and through the flexible metal tubes themselves may be a conductive fluid such as saline. Physiological saline may help minimize the detrimental effects associated with the introduction of large amounts of fluid to the vascular system by maintaining a relatively constant electrolyte balance within the blood.

Although a conductive fluid such as saline is described, the fluid flowing within and among the tubes, may be any type of fluid capable of flowing through the interstitial spaces and/or flexible metal tubes. For instance, conductive fluids other than saline, non-conductive fluids, therapeutic agents, or medicines could also be provided to the working surface if desired.

Figure 8:
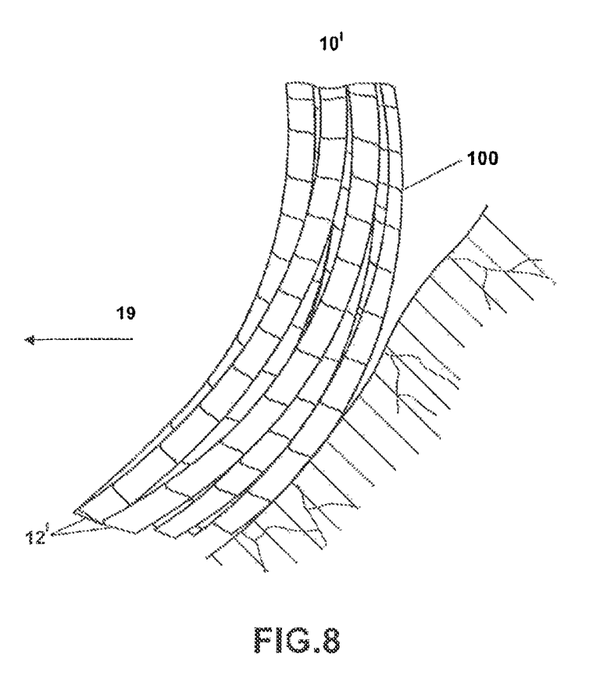
FIG. 8 shows a bundle of flexible metal tubes with spiral cuts making contact with a tissue surface in a manner that bends the tubes along their longitudinal axes.

The flexible metal tubes 12 of the conforming electrode 10 are constructed to be flexible such that when they come into contact with tissue, the conforming electrode 10 is deflected in direction 19 as illustrated in FIG. 8, thereby increasing the contact surface between the conforming electrode 10 and the tissue. Advantageously, this increased contact surface improves the efficacy of, for example, the delivery of ablating energy to the tissue.

An irrigated electrode such as a "wet brush" conforming electrode as described may advantageously enhance cooling of both the electrode and the tissue being treated. The coolant flowing through the fluid passageways provided by the interstitial spaces and hollow tube interiors cool the electrode first, and then cool the adjacent tissue by thermal conduction. The flexibility of the irrigated electrode permits it to more closely conform to the tissue surface. This conformance increases the contact area between the electrode and the tissue being treated, which in turn enhances conductive heat transfer from and cooling of the tissue.

The manufacture of the flexible metal tubes may be accomplished by a variety of known manufacturing techniques. For instance, the flexible metal tubes may be formed through an extrusion process. The extrusion may produce a solid metal fiber, which is later hollowed, or may directly extrude a hollow tube. One of skill in the art will appreciate that any of a number of methods for making flexible metal tubes may be chosen depending on the characteristics of the material being used and the specific physical properties desired for the tubes.

While the use of flexible metal tubes provides a number of instant advantages over other types of filaments, they also present design challenges. Hollow tubes for use according to the present teachings can be difficult to manufacture. For instance, the hollowing of the filaments to create tubes may affect the flexibility and/or elasticity of the filaments themselves. Metal tubes may also become susceptible to "kinking" which can restrict the flow of fluids through the tubes. "Kinking" may also compromise the structural integrity of the tubes.

Figure 7:
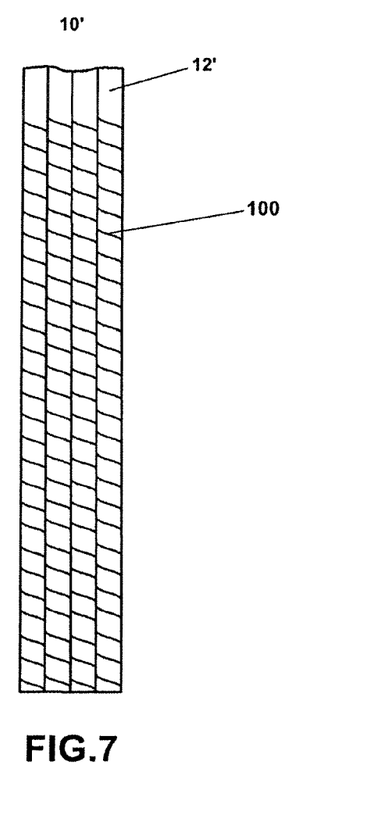
FIG. 7 depicts a bundle of flexible metal tubes with spiral cuts along their longitudinal axes.

FIG. 7 illustrates an embodiment of flexible metal tubes 12' for use in a conforming electrode 10' which overcomes some of the shortcomings of flexible metal tubes just described. The flexible metal tubes 12' shown in FIG. 7 are provided with spiral cuts 100 through the walls of the tubes along a longitudinal axis. Preferably, the spiral cuts 100 are made at an angle of 60° C. off the longitudinal axis of the tube and extend from the most distal end of the tube to a point near the proximal end of each tube. Generally, an angle of about 40° to about 70° is preferred, though other angles may be used for the spiral cut.

The addition of spiral cuts through the tubes provides a number of additional mechanical and thermodynamic advantages.

First, the addition of spiral cuts increases the flexibility of the individual tubes in a manner that also alleviates the "kinking" problem associated with the bending of simple metal tubes. Second, the addition of spiral cuts may also enhance the elasticity or resiliency of each metal tube after it has been flexed. The addition of a spiral cut introduces a "spring-type" mechanism to the tube, which helps the tube return to its original shape after it has been deflected (as in FIG. 8).

In addition to the mechanical advantages conferred by the addition of spiral cuts, a thermodynamic improvement is also obtained. The addition of spiral cuts along the entire longitudinal axes of each metal tube provides additional surface area through which cooling fluid may be introduced in a relatively slow and controlled manner. The geometry of spirals along a longitudinal axis allow for cuts along the axis that are effectively longer than the tubes themselves. These spiral cuts introduce additional exposed surfaces through which cooling fluid flowing through the hollow tubes may gradually escape, further improving the efficiency of the cooling fluid while still effectively managing the total volume of fluid introduced to the area.

It is contemplated that spiral cuts at various pitches and angles other than 60° may be desirable depending on the desired characteristics. For instance, providing spiral cuts which introduce more revolutions of the tube along its length could increase the flexibility of the tube and the amount of fluid provided to the working surface. Additionally, spiral cuts need not be continuous along the entire tube. A single spiral cut section along a particular length of tube or a plurality of shorter spiral cuts along a tube may be desirable in some applications. It may also be desirable to provide spiral cuts along some tubes but not others, depending on their location within a bundle. By providing spiral cuts to only some sections along the lengths of the tube, the flexible portions of the conforming electrode may be tailored to the particular application. Moreover, while a single spiral cut running along the majority of the length of the tube is preferred, it is contemplated that multiple spiral or arcuate cuts of varying lengths may be made. For example, each tube may have two spiral cuts spaced apart from each other.

It is contemplated that the flexible metal tubes of the conforming electrode described may be secured by welding the tubes. In a particular embodiment, the welding may be laser welding. The availability of welding (including, for example, laser welding) to secure the flexible metal tubes of the present teachings constitutes another advantage of using metal tubes. Welding offers increased strength and reliability to the attachment of each filament in the conforming electrode. The flexible metal tubes may be welded to each other during manufacture to help secure the bundle of filaments. Alternatively, the filaments may be individually welded to an attachment point on a surgical device. Additionally, the filaments may be both welded to each other and to a secure attachment point in order to provide extra strength and reliability.

Figure 9:
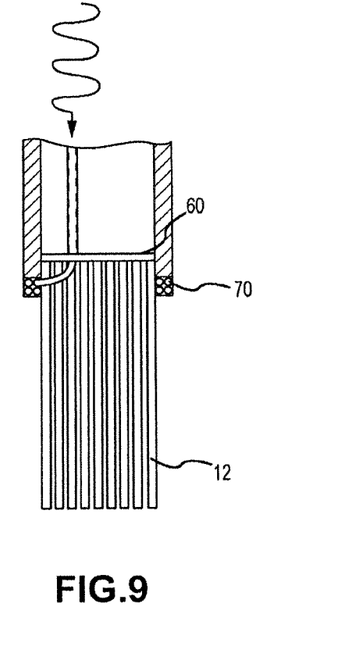
FIG. 9 depicts a longitudinal cross-sectional view through a conforming electrode showing the individual flexible metal tubes, a primary conduction wire looped around the outer perimeter of the conforming electrode, and a mounting means for attaching the tubes.

FIG. 9 illustrates an embodiment showing several of the alternatives for welding attachments of the individual metal tubes. In FIG. 9, each of the individual metal tubes 12 may be welded to one or more other, adjacent tubes, as described above. Alternatively (or additionally) the individual tubes may be welded at various attachment points. An anchor means 60 may be provided within the shaft of the catheter or surgical instrument. The anchor may be made of a suitable metal or other material, and is preferably suitable for welding to the flexible metal tubes. FIG. 9 also illustrates a primary conduction wire 70, which wraps around the circumference of the bundle of metal tubes. One purpose of the primary conduction wire is to provide the ablative energy to the conforming electrode. However, because the conduction wire is probably formed from metal, the material of the primary metal conduction wire may be chosen to provide a suitable welded joint between the tubes along the outer perimeter of the bundle and the conduction wire. One of skill in the art will appreciate that there are a number of different elements and designs that could be introduced to the distal end of a catheter to provide welding points for the metal tubes.

As discussed above, the strength of the attachment of each of the filaments and the ability to account for each and every filament introduced into and removed from the vascular environment are important considerations for designing a safe and effective conforming electrode. The present conforming electrode employing flexible metal tubes effectively balances the competing design requirements by providing filaments comprised of flexible metal tubes which may be individually welded to each other and various attachment points on a catheter. Additionally, the incorporation of tubes with helical cuts along the longitudinal axes of the metal tubes provide such significantly improved thermal and electrical characteristics to the tubes as to allow for a significantly reduced number of fibers when compared to previous conforming electrodes. The concomitant reduction in the number of fibers required to provide comparable thermal and electrical performance permits individual accountability of each fiber and its attachment to the catheter, thereby enhancing the safety of conforming electrodes intended for vascular applications.

In addition, the conforming electrode comprising flexible metal tubes could include one or more sensors as described in U.S. application Ser. No. 10/808,919, filed 24 Mar. 2004 ("the '919 application"), or U.S. application Ser. No. 11/617,397, filed 28 Dec. 2006 ("the '397 application"). Both the '919 application and the '397 application are hereby incorporated by reference as though fully set forth herein.

Figure 10:
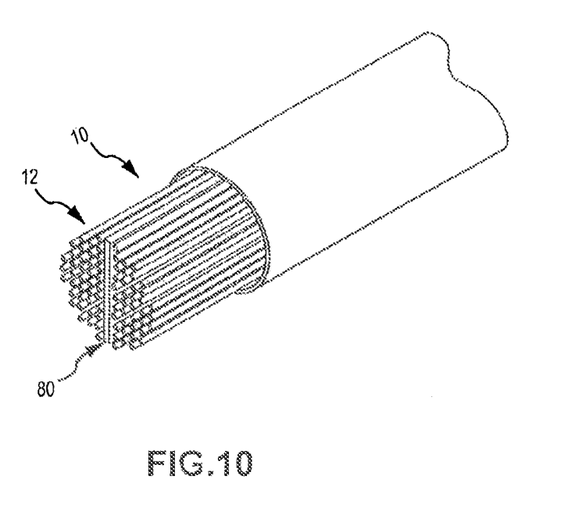
FIG. 10 is a cross-sectional view of a conforming electrode having a device (e.g., a thermocouple or other temperature sensor, a pressure sensor, or an ultrasound sensor) embedded among the flexible metal tubes.
Figure 11:
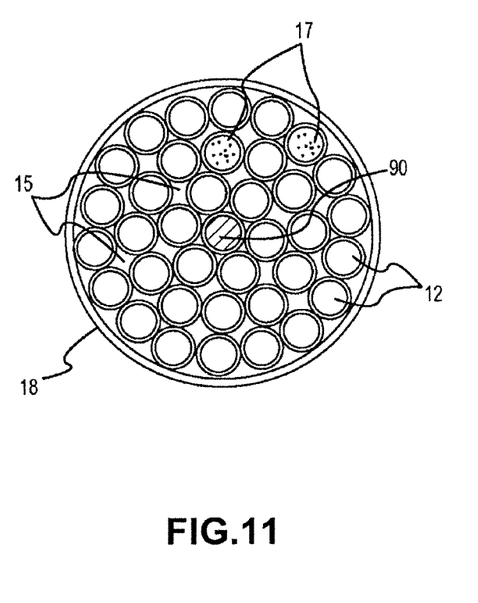
FIG. 11 is a cross-sectional view of a conforming electrode having a device (e.g., a thermocouple or other temperature sensor, a pressure sensor, or an ultrasound sensor) embedded within the flexible metal tubes themselves.

Sensors for use in the present teachings may include electrical sensors, thermal sensors, and/or contact sensors. However, any sensor desired or appropriate for the working end of a catheter may be accommodated. The sensors may be embedded among the flexible metal tubes in a manner similar to what is described and shown in the '919 and '397 applications. For instance, FIG. 10 illustrates a piezoelectric contact sensor 80 embedded among the plurality of flexible metal tubes 12. Additionally, it is specifically contemplated that the sensors could be incorporated into the flexible metal tubes themselves. As an example, in FIG. 11 a piezoelectric sensor or thermocouple 90 could be incorporated into the hollow portion of an individual flexible metal tube. The metal tubes incorporating sensors may be individually designed, sized, and placed in a manner that does not depart from the scope of the present teachings.

It should be noted that although the flexible tubes according to the present teachings are depicted in nearly all of the figures as having circular cross sections for visual simplicity, the individual tubes may intentionally or unintentionally have a wide variety of cross-sectional configurations and areas, and need not be circular. Manufacturing irregularities may result in various cross-sectional configurations, or tubes having a variety of different cross-sectional configurations may be intentionally selected to achieve a desired electric field at the electrode-tissue interface. The tubes also may not be perfectly aligned longitudinally. Further, the tubes may comprise an arrangement of braided or twisted groups of tubes, or comprise a roving pattern of untwisted, longitudinally-extending, substantially-parallel, conductive and nonconductive tubes.

Although several embodiments of this invention have been described above with a certain degree of particularity, those skilled in the art could make numerous alterations to the disclosed embodiments without departing from the scope of this invention. For example, a catheter formed according to the present teachings may have varying sizes and varying uses, including, but not limited to, the treatment of atrial fibrillation and the treatment of atrial tachycardia.

One of ordinary skill in the art will also appreciate that other modifications could be made to the catheter assembly herein without departing from the scope of the present invention. For example, the conforming electrode comprising flexible metal tubes could be made in a manner such as described in the '919 or the '397 application using any of the configurations described therein with filaments comprising materials other than flexible metal tubes.

In addition, it is contemplated that a catheter according to the present invention may be manufactured using alternative techniques. For instance, the helical cuts may be manufactured using laser cutting or mechanical cutting. As previously described, the welding of individual tubes may be accomplished by laser welding or other welding techniques. However, other means of secure attachment such as adhesives or mechanical means may be effectively used.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the invention as defined in the appended claims.

What is claimed is:

1. A conforming electrode for delivering ablative energy to tissue, the conforming electrode comprising the following:
    a plurality of flexible metal tubes, each of the plurality of flexible metal tubes having a longitudinal axis, a proximal end, and a distal end;
    wherein at least some of the plurality of flexible metal tubes have helical cuts along the longitudinal axis of the tubes;
    said flexible metal tubes arranged in a bundle with the longitudinal axes of the flexible metal tubes being aligned parallel, and wherein a plurality of nonconductive tubes are interspersed with the flexible metal tubes; and
    said flexible metal tubes electrically coupled to a conductor for transferring ablative energy to the flexible metal tubes; and
    a catheter shaft having a distal end and a sheath coupled to the distal end of the catheter shaft,
    wherein the proximal ends of the plurality of flexible metal tubes are secured to the distal end of the catheter shaft, and
    wherein the sheath is configured to be extendable over the plurality of flexible metal tubes.

2. The conforming electrode of claim 1, wherein the flexible metal tubes are comprised of a shape memory material.

3. The conforming electrode of claim 2, wherein the metal is nickel titanium.

4. The conforming electrode of claim 1, wherein the proximal ends of at least some of the plurality of flexible metal tubes are secured to the proximal ends of other flexible metal tubes.

5. The conforming electrode of claim 4, wherein the proximal ends of at least some of the plurality of flexible metal tubes are welded to the proximal ends of other flexible metal tubes.

6. The conforming electrode of claim 5, wherein the welding comprises laser welding.

7. The conforming electrode of claim 1, wherein the conductor forms a loop around the plurality of flexible metal tubes and the plurality of flexible metal tubes are additionally secured to the conductor loop.

8. The conforming electrode of claim 7, wherein the proximal ends of at least some of the plurality of flexible metal tubes are secured to the proximal ends of other flexible metal tubes.

9. The conforming electrode of claim 1, further comprising:
    an electrode housing coupled to the distal end of the catheter shaft; wherein the proximal ends of at least some of the plurality of flexible metal tubes are secured to the proximal ends of other flexible metal tubes, and said proximal ends of the at least some of the plurality of flexible metal tubes are also secured to the electrode housing.

10. The conforming electrode of claim 9, wherein the electrode housing is a conductive sheath.

11. The conforming electrode of claim 1, wherein the helical cuts are continuous along the longitudinal axes of the flexible metal tubes from the distal end of the tubes to a point near the proximal ends of the flexible metal tubes.

12. The conforming electrode of claim 1, wherein the helical cuts comprise a plurality of non-continuous cuts along the longitudinal axes of the flexible metal tubes.

13. The conforming electrode of claim 1 wherein the plurality of flexible metal tubes are arranged in a bundle which form interstitial spaces between the flexible metal tubes.

14. The conforming electrode of claim 13 further comprising a fluid lumen that is adapted to deliver fluid to the interstitial spaces between the flexible metal tubes.

15. The conforming electrode of claim 1 further comprising:
a fluid lumen in the catheter shaft to deliver a fluid;
a manifold coupled to the fluid lumen and coupled to at least some of the plurality of flexible metal tubes to deliver a fluid to the plurality of flexible metal tubes.

16. The conforming electrode of claim 1, further comprising a sensor embedded among the plurality of flexible metal tubes.

17. The conforming electrode of claim 16, wherein the sensor comprises an electrical, thermal or contact sensor.

18. The conforming electrode of claim 1, further comprising a sensor embedded within at least one of the plurality of flexible metal tubes.

19. An ablation catheter comprising the following:
an ablating electrode comprising a plurality of flexible metal tubes, each of the plurality of flexible metal tubes having a longitudinal axis, a proximal end, a distal end, and a tubular wall;
at least some of said flexible metal tubes having helical cuts extending through the tubular walls of said flexible metal tubes along the longitudinal axes of said flexible metal tubes;
said flexible metal tubes arranged in a bundle with the longitudinal axes of said flexible metal tubes being aligned parallel;
said flexible metal tubes electrically coupled to a conductor for transferring ablative energy to said flexible metal tubes;
a catheter shaft having a distal end and a sheath coupled to the distal end of the catheter shaft,
wherein the proximal ends of the plurality of flexible metal tubes are secured to the distal end of the catheter shaft, and
wherein the sheath is configured to be extendable over the plurality of flexible metal tubes; and an electrode housing coupled to the distal end of the catheter shaft; wherein the proximal ends of at least some of the plurality of flexible metal tubes are secured to the proximal ends of other flexible metal tubes, and said proximal ends of the at least some of the plurality of flexible metal tubes are also secured to the electrode housing.

20. A conforming electrode for delivering ablative energy to tissue, the conforming electrode comprising the following:
a plurality of flexible metal tubes, each of the plurality of flexible metal tubes having a longitudinal axis, a proximal end, and a distal end;
wherein at least some of the plurality of flexible metal tubes have helical cuts along the longitudinal axis of the tubes;
said flexible metal tubes arranged in a bundle with the longitudinal axes of the flexible metal tubes being aligned parallel; and
said flexible metal tubes electrically coupled to a conductor for transferring ablative energy to the flexible metal tubes; and
a catheter shaft having a distal end and a sheath coupled to the distal end of the catheter shaft,
wherein the proximal ends of the plurality of flexible metal tubes are secured to the distal end of the catheter shaft,
wherein the sheath is configured to be extendable over the plurality of flexible metal tubes, and
wherein the conductor forms a loop around the plurality of flexible metal tubes and the plurality of flexible metal tubes are additionally secured to the conductor loop.

* * * * *